United States Patent
Stening et al.

(10) Patent No.: US 10,810,847 B2
(45) Date of Patent: Oct. 20, 2020

(54) METHOD AND CAMERA SYSTEM COMBINING VIEWS FROM PLURALITY OF CAMERAS

(71) Applicant: Axis AB, Lund (SE)

(72) Inventors: Johan Stening, Lund (SE); Hampus Linse, Lund (SE); Song Yuan, Lund (SE)

(73) Assignee: Axis AB, Lund (SE)

( * ) Notice: Subject to any disclaimer, the term of this patent is extended or adjusted under 35 U.S.C. 154(b) by 0 days.

(21) Appl. No.: 16/525,096

(22) Filed: Jul. 29, 2019

(65) Prior Publication Data

US 2020/0035075 A1 Jan. 30, 2020

(30) Foreign Application Priority Data

Jul. 30, 2018 (EP) ..................................... 18186340

(51) Int. Cl.
*G08B 13/196* (2006.01)
*H04N 5/232* (2006.01)

(52) U.S. Cl.
CPC . *G08B 13/19608* (2013.01); *G08B 13/19606* (2013.01); *G08B 13/19641* (2013.01); *H04N 5/23238* (2013.01)

(58) Field of Classification Search
None
See application file for complete search history.

(56) References Cited

U.S. PATENT DOCUMENTS

| 9,760,768 B2 | 9/2017 | Macmillan et al. |
| 2004/0247173 A1 * | 12/2004 | Nielsen ................. G06T 3/0062 382/154 |
| 2013/0278727 A1 * | 10/2013 | Tamir .................. H04N 13/261 348/47 |

(Continued)

FOREIGN PATENT DOCUMENTS

WO 2010/044913 A1 4/2010

OTHER PUBLICATIONS

Helala et al., "Mosaic of Near Ground UAV Videos under Parallax Effects," 2012 Sixth International Conference on Distributed Smart Cameras (ICDSC), Hong Kong, pp. 1-6 (2012).

(Continued)

*Primary Examiner* — Fernando Alcon
(74) *Attorney, Agent, or Firm* — Volpe and Koenig, P.C.

(57) ABSTRACT

A method and a camera system for stitching video data from two image sensors arranged to each capture video data of overlapping camera views comprises detecting motion in an area in the camera views corresponding to the overlapping camera views,
determining an activity distance, being the distance from a position at the location of the two image sensors to an activity position including the detected motion, positioning in a three-dimensional coordinate system a predefined projection surface at a position having a distance between the position at the location of the image sensors and a position of the projection of the activity onto the projection surface that corresponds to the determined activity distance, projecting the video data from each of the image sensors onto the predefined projection surface that have been positioned at the activity distance, and outputting a two-dimensional video corresponding to the projection onto the projection surface.

15 Claims, 7 Drawing Sheets

(56) References Cited

U.S. PATENT DOCUMENTS

| | | | | |
|---|---|---|---|---|
| 2018/0139431 A1* | 5/2018 | Simek | .................. | H04N 13/232 |
| 2019/0230285 A1* | 7/2019 | Kim | ..................... | H04N 19/134 |
| 2019/0289206 A1* | 9/2019 | Kawaguchi | ........... | G06T 3/0062 |
| 2019/0289302 A1* | 9/2019 | Abbas | .................. | H04N 19/147 |
| 2019/0306420 A1* | 10/2019 | Okaki | .................. | H04N 5/2258 |
| 2020/0021791 A1* | 1/2020 | Hur | .................. | H04N 21/26258 |
| 2020/0029025 A1* | 1/2020 | Yokota | .................... | G06T 17/00 |

OTHER PUBLICATIONS

Saldanha, "The Differences Between MultiSensor and Fisheye Panoramic Cameras," Security Sales and Integration, Available at: https://www.securitysales.com/in-depth/differences-multi-sensor-fisheye-cameras/ (Oct. 6, 2017).

Extended European Search Report dated Jan. 18, 2019 for the European Patent Application No. 18186340.8.

* cited by examiner

METHOD AND CAMERA SYSTEM COMBINING VIEWS FROM PLURALITY OF CAMERAS

TECHNICAL FIELD

The present invention relates to a method and a camera system for stitching video from a plurality of cameras.

BACKGROUND

In some monitoring systems it is interesting to monitor a large area in its entirety, i.e. not just smaller portions of the area. This may be accomplished using a wide-angle lens such as a fisheye lens. However, that kind of setup may provide a video having lower resolution than required by the party interested in monitoring the area or it may be too expensive. An alternative to the fisheye lens arrangement is to arrange two or more cameras each capturing a video stream of a portion of the area to be monitored and then to stitching the videos together into one single video stream. In FIG. 1 an example is shown of two cameras 102, 104 that together is monitoring an area 105 larger than they are able to monitor individually.

Each camera is individually directed in a direction 106, 108, respectively, and captures a view being a portion of the entire scene 105 of the monitored area. FIG. 2 depicts the camera view from camera 102 and FIG. 3 depicts the camera view from camera 104. The cameras may be directed in parallel as in the figure or they be directed in different directions as long as they together represent the larger area 105. In fixed camera installations it would be desirable to have the video captured by camera 102 connect exactly to the video captured by camera 104.

However, an alignment between the two cameras and their respective captured scene that is so exact that the combination of the scenes becomes seamless is essentially impossible to achieve and to maintain. Therefore, the cameras 102, 104, covering an area are arranged to overlap in capturing the scene. In the present application overlapping scenes should be interpreted as meaning that the scene captured by one digital video camera 102 of a plurality of digital video cameras 102, 104, includes a portion of the scene captured by another digital video camera 104. This, overlap 110 is depicted in FIG. 4, showing the images of FIG. 2 and FIG. 3 stitched together and the area of the scene that is common 110 for the two images and is the overlap area 110 is indicated by hash lines. To expand the viewing area by stitching two videos in this way is quite common and there are plenty of known methods to achieve this.

However, there is a problem in the stitched image in FIG. 4, representing a stitched video. The house in the background is blended in at different positions as the two images are aligned in respect of the road in the foreground. The house captured by camera 102 being the house marked as 112 and the house captured by camera 104 being the house marked as 114. The reason for the house being positioned differently is that the two cameras 102, 104, is arranged at a distanced from each other. The distance d between the two cameras results in that the two cameras does not capture the scene from the same point and thereby there will be parallax in the resulting image. Parallax in overlaid images results in an apparent displacement of an object as seen from two different viewing points.

One way to solve this is to set up the cameras and make the system identify features in the overlap area. From these features then calculate an adjustment matrix that when applied to the image data of the overlap compensate for and substantially remove all parallax problems in the video by individually adjusting each pixel in a frame of the video. There is however a drawback with such an approach. The calculations needed to generate the adjustment matrix are very computationally intensive and therefore not practical to run on a system having limited processing power, e.g. a network camera, a networked video encoding device or a networked video processing device connected to a plurality of cameras for processing video from these cameras. Moreover, cameras may be slightly redirected during their normal day operation as they are exposed to harsh weather conditions or by impact from activities in the area surrounding the camera. In case of the cameras being slightly redirected a new adjustment matrix has to be calculated.

SUMMARY

A stitching method requiring low processing power and still deliver acceptable video of the overlap area would be desirable.

A method for stitching video data from two image sensors is set forth according to claim 1 and by means of camera system according to claim 12. Further embodiments are presented in the dependent claims.

In particularly, according to embodiments, the method for stitching video data from two image sensors arranged to each capture video data of overlapping camera views, comprises detecting motion in an area in the camera views corresponding to the overlapping camera views, determining an activity distance, being the distance from a position at the location of the two image sensors to an activity including the detected motion, positioning in a three-dimensional coordinate system a predefined projection surface at a position having a distance between the position at the location of the image sensors and a position of the projection of the activity onto the projection surface that corresponds to the determined activity distance, projecting the video data from each of the image sensors onto the predefined projection surface that have been positioned at the activity distance, and outputting a two-dimensional video corresponding to the projection onto the projection surface.

One advantage of projecting the video data from the two sensors on a projection surface positioned in the three-dimensional coordinate system at a distance from the camera corresponding to the distance to detected activity is that the good viewing experience of the stitched video may be enabled using limited processing resources. The processing power is possible to keep at a low level due to the use of a projecting surface and then the experienced quality of the video is enhanced by compromising in the video experience by selectively avoiding parallax effects in a region of motion, which is a region an operator or viewer of the video will focus.

In other embodiments the detecting of motion in an area in the camera views corresponding to the overlapping camera views includes detecting moving pixels in an overlapping portion of the captured video. One advantage of this feature is that the motion detection may be accomplished in the video processing device and facilitate the positioning of features moving in the video.

In further embodiments the method may further comprise determining from pixel data in the overlapping camera views the activity position of the detected motion and using this activity position in the determining of the activity distance.

In yet other embodiments the determining of an activity position is based on a momentaneous instance of the detected motion in the overlapping image data and setting the position of the motion as the activity position. The advantage of this is that the viewing experience may be improved for scenes wherein the interesting areas of the scene including motion is occurring at different distances from the camera. In particular if the variation of distance to moving features or objects in the scene tend to vary frequently.

In yet other embodiments the determining of an activity position includes accumulating motion data in the overlapping image data during a predetermined time period and then selecting a position that have accumulated most motion during this time period as the activity position. In this way the viewing experience may be improved for scenes where the distance to the moving features or objects tends to vary from a quite stable base distance.

Further, some embodiments include determining the activity distance includes comparing the position of the activity position in the captured video data with corresponding positions in a predetermined table including distances to positions in a coordinate system of each of the image sensors. This may even further decrease the processing power required for providing the improved viewing experience.

In yet other embodiments the determining of the activity distance includes receiving a radar signal covering the overlapping scenes, correlating a radar response to the activity position, and retrieving the distance to the activity position from the radar signal.

Further in some embodiments determining the activity distance includes calculating the difference, $x_1-x_2$, in position of the activity position in the captured images from the two sensors.

In some embodiments the projection surface may be a plane, in others projection surface may be a cylindrical surface, and in others yet the projection surface may be a spherical surface.

According to another aspect a camera system comprises two cameras, each including an image sensor, at least one image processing device, a predetermined projection surface defined in a three-dimensional coordinate system, motion detector configured to identify motion in overlapping camera views of the two cameras, activity distance determining module configured to determining the activity distance a being the distance from a position at the location of the two image sensors to an activity, the activity being a motion detected in video data from the two cameras in overlapping camera views of these cameras, an image projector configured to project video data captured using the cameras onto a projection surface positioned in a three-dimensional coordinate system at a position having a distance between the position at the location of the image sensors and a position of the projection of the activity onto the projection surface that corresponds to the determined activity distance, output configured to deliver the video data produced by the image projector as stitched video from the two cameras.

One advantage of having the image projector projecting the video data from the two sensors on the projection surface positioned in the three-dimensional coordinate system at a distance from the camera corresponding to the distance to detected activity is that the good viewing experience of the stitched video may be enabled using limited processing resources. Further, it is possible to keep the processing power at a low level due to the use of a projecting surface and then the experienced quality of the video is enhanced by compromising in the video experience by selectively avoiding parallax effects in a region of motion, which is a region an operator or viewer of the video will focus.

In other embodiments the motion detector is configured to detect moving pixels in the overlapping portion of the video data from the cameras. One advantage of this feature is that the motion detection may be accomplished in the video processing device and facilitate the positioning of features moving in the video.

In yet other embodiments the camera may further comprise a motion accumulator connected to the motion detector for accumulating detected motions during a predetermined period of time and wherein the activity distance determining module is configured to determine the activity distance from the accumulated detected motions. By means of the motion accumulator the viewing experience may be improved for scenes where the distance to the moving features or objects tends to vary from a quite stable base distance.

Further, the image projector may be configured to project video data onto a plane projection surface.

A further scope of applicability will become apparent from the detailed description given below. However, it should be understood that the detailed description and specific examples, while indicating preferred embodiments, are given by way of illustration only, since various changes and modifications will become apparent to those skilled in the art from this detailed description. Hence, it is to be understood that the teachings are not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a sensor" or "the sensor" may include several sensors, and the like. Furthermore, the word "comprising" does not exclude other elements or steps.

BRIEF DESCRIPTION OF THE DRAWINGS

Other features and advantages will become apparent from the following detailed description of a presently preferred embodiment, with reference to the accompanying drawings, in which.

Further, in the figures like reference characters designate like or corresponding parts throughout the several figures.

DETAILED DESCRIPTION OF EMBODIMENTS

The present teachings relate to stitching of images captured by cameras positioned at predetermined and fixed positions.

Figure 5:
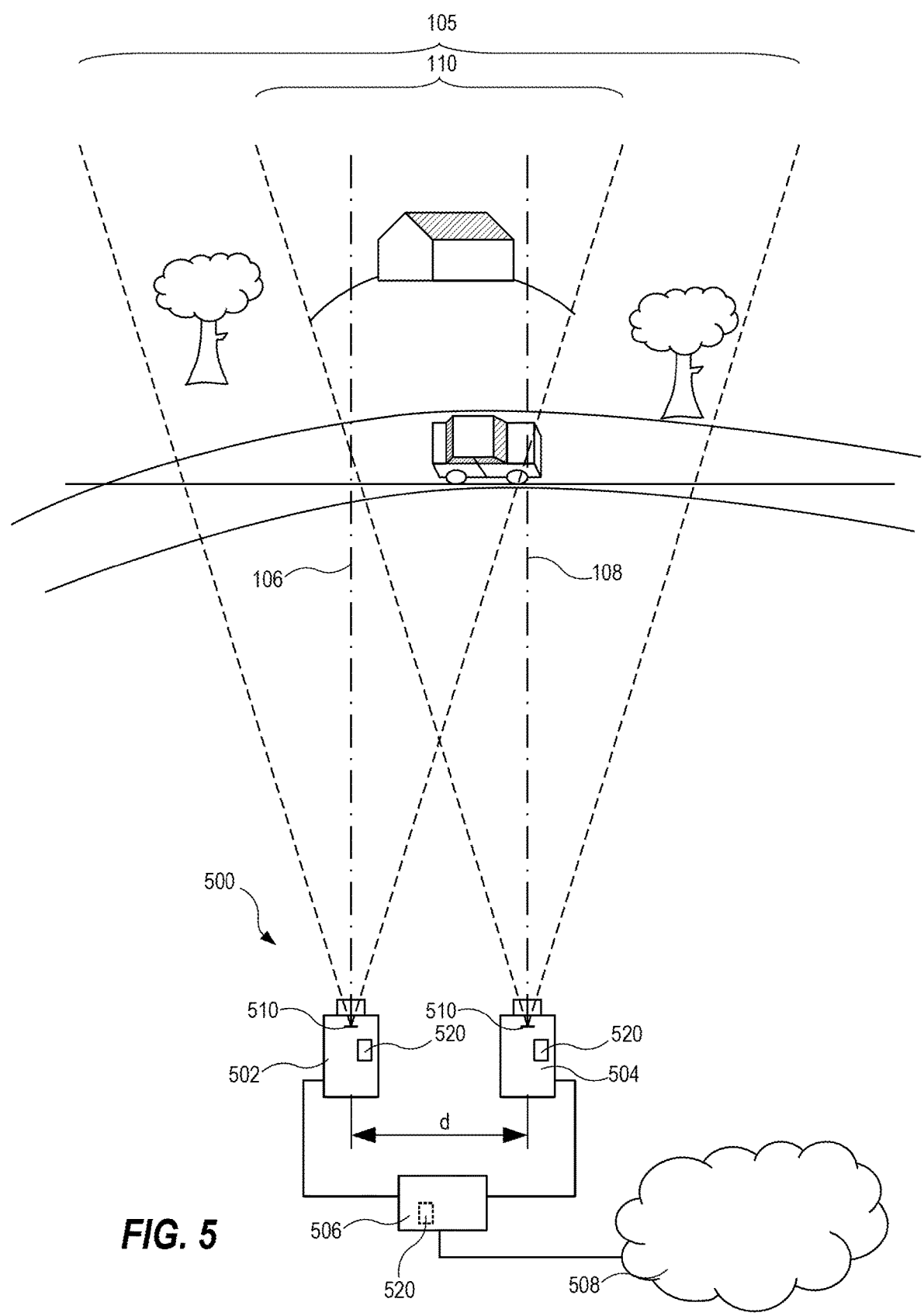
FIG. 5 is a schematic overview of a camera system according to embodiments capturing the same scene as the setup in FIG. 1.

Now referring to FIG. 5, showing a system 500 for capturing and stitching images. The system 500, implementing an embodiment, may include two digital video cameras 502, 504, mounted to capture digital image data of overlapping scenes. Overlapping scenes is intended to mean that the scene captured by one 502 of the digital video cameras 502, 504, includes a portion of the scene captured by the other digital video camera 104. This common portion of the scene captured is hereinafter referred to as video overlap 110. The two cameras capture images which in combination represents a total scene 105. The digital video cameras 502, 504, are mounted at specific distance d from each other and the direction, 106, 108, of an optical axis of each of the cameras may also be well known. In FIG. 5 the optical axis of the cameras 502, 504 are parallel, but it is not necessarily the case. The embodiments will also work for arrangements in which the cameras are directed at diverging angles between their respective optical axis as long as a video overlap is produced. Each of the digital video cameras 502, 504, may be synchronised in time or at least the information of any difference in timing between the cameras are made available to an image processing device 506. The images captured by the cameras 502, 504, are transmitted to the image processing device 506. At the image processing device 506 the images are stitched together to a total scene 105 and collected in a video sequence. A video or a video sequence is formed from a sequence of temporally consecutive images in order to enable registration and play back of activities captured in the camera view. The video or video sequences may be encoded using a combination spatial and temporal encoding schemes, e.g. I-frames and P-frames. Examples of such encoding schemes are Mpeg-2, Mpeg-4, H.264, H.265, etc. Then the stitched video sequence may be transmitted and/or streamed to a storage device, e.g. an internal memory card or hard drive, an external Network Attached Storage, a video server, a client computer, a video management system, etc. The transmission to storage devices external to the image processing device may be performed via a network 508 such as, for example, the Internet, a Local Area Network, a Wide Area Network, a cellular network, a public switched telephone network, etc. Each digital video camera 502, 504, includes an image sensor 510 arranged to register light from the scene and to convert the registered light to image data representing the captured scene.

Figure 6:
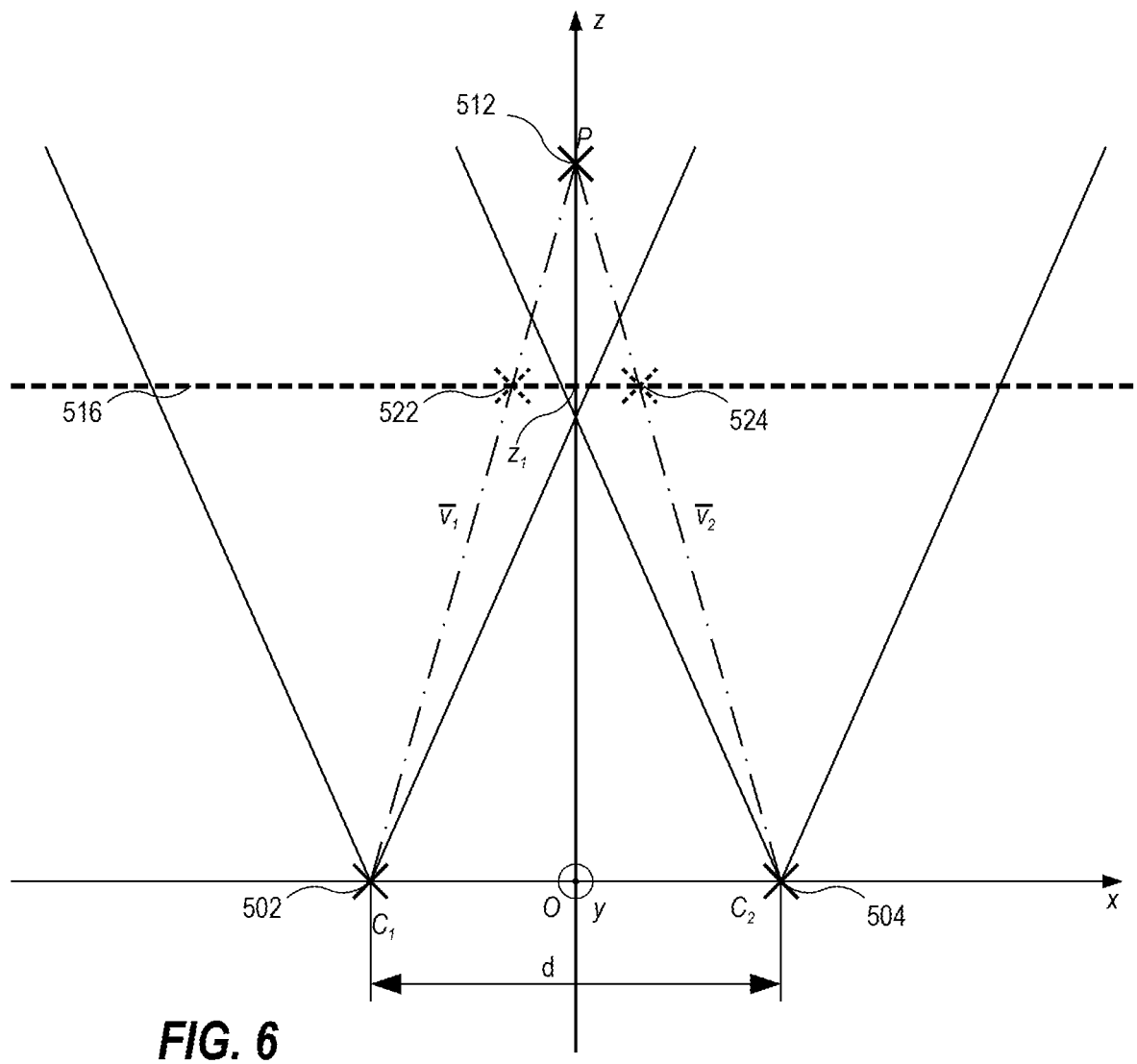
FIG. 6 is a schematic view of two camera views and image projection of an object.

Now referring to FIG. 6, according to some embodiments, the image data from each sensor 510 is being captured and registered in a local 2-dimensional coordinate system of each camera 502, 504, e.g. the 2-dimensional coordinate system being related to the surface of the image sensor 510 which is a 2-dimensional plane. The system implements and operates within a 3-dimensional coordinate system in which the pixels of the image sensor plane are mathematically projected on to a projection surface 516, e.g. a plane, in a 3-dimensional space represented in the 3-dimensional coordinate system. The coordinate system of the video capturing system 500 may be a cartesian coordinate system having an x-, y-, and z-axis, all originating in the origin O, where all the axes of the coordinate system intersects. The image data of each of the image sensors of the cameras 502, 502, may be converted into this 3-dimensional coordinate system by projecting them onto the projection surface 516 at a distance $z_1$ from the camera system, in this example from the origin O. Each camera may alternatively have an individual distance to individual projection surfaces onto which the image data of each camera is projected. The projection surface 516 may be a plane, as in FIG. 6, a part of a cylinder, a part of a sphere, or any other shape that the skilled person would consider. In some embodiments the distance $z_1$ is initially a predetermined distance which is the same for the projection surface 516 of the image data from both cameras 502, 504, which is depicted in FIG. 6. The position of each of the digital video cameras 502, 504, is denoted $C_1$ and $C_2$, respectively, and are in the area of the origin O of the 3-dimensional coordinate system. In this example, each of the cameras 502, 504, have its optical axis in the plane of the x- and z-axis. The distance d between the cameras 502, 504, is well known and thereby the positions $C_1$ and $C_2$ in the 3-dimensional coordinate system are well known.

Figure 7:
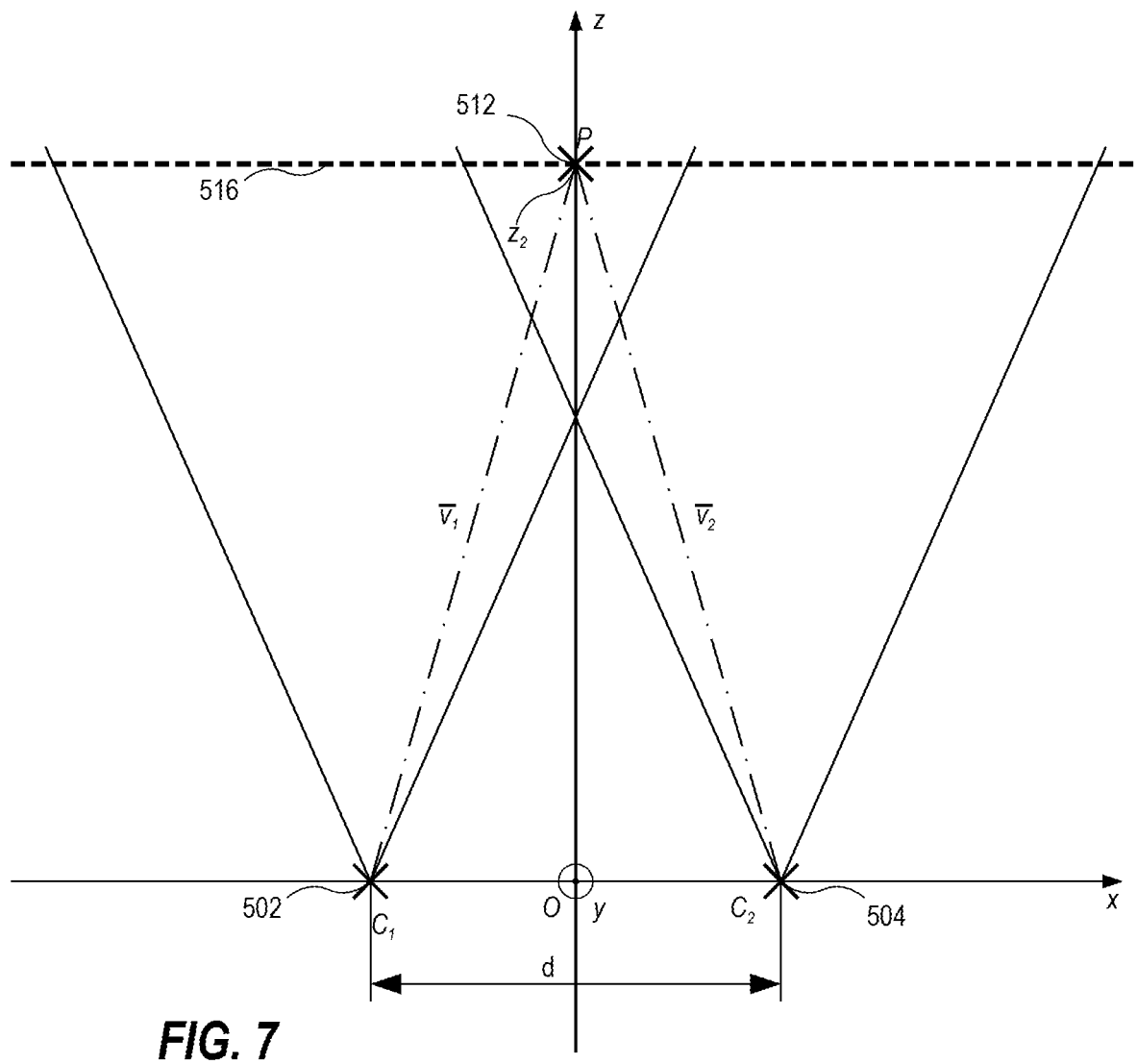
FIG. 7 is a schematic view of the two camera views of FIG. 6 having the distance to the projection altered.

In FIG. 6 an object 512 is present in the scene at the position P in the 3-dimensional coordinate system. Each of the image sensors register the object, as it is positioned in the overlap of the scenes captured by the camera, and the image from each sensor is projected onto the projection surface 516. The projection of the object 512 as captured by the camera 502 is visualized by the symbol X having reference numeral 522 and the projection of the object 512 as captured by the camera 504 is visualized by the symbol X having reference numeral 524. It is evident from figure that the projection of the object 512 experience parallax problems as the data from one camera places the object at one position on the projection surface and the data from the other camera places the object at a different position on the projection surface. This parallax problem may be avoided by moving the projection surface 516 to the position P of the object 512, i.e. positioning the projection surface 516 so that it intersects the position P of the object 512. The resulting diagram is shown in FIG. 7. The projection of object 512 does not present any parallax artefacts as both cameras 502, 504, projects the object 512 at the same position on the projection surface 516. As seen from the figure, the projection surface 516 has been moved to a distance $z_2$ from the origin, which distance corresponds to the position P of the object 512 along the z-axis in the 3-dimensional coordinate system of the camera system 500.

Figure 1:
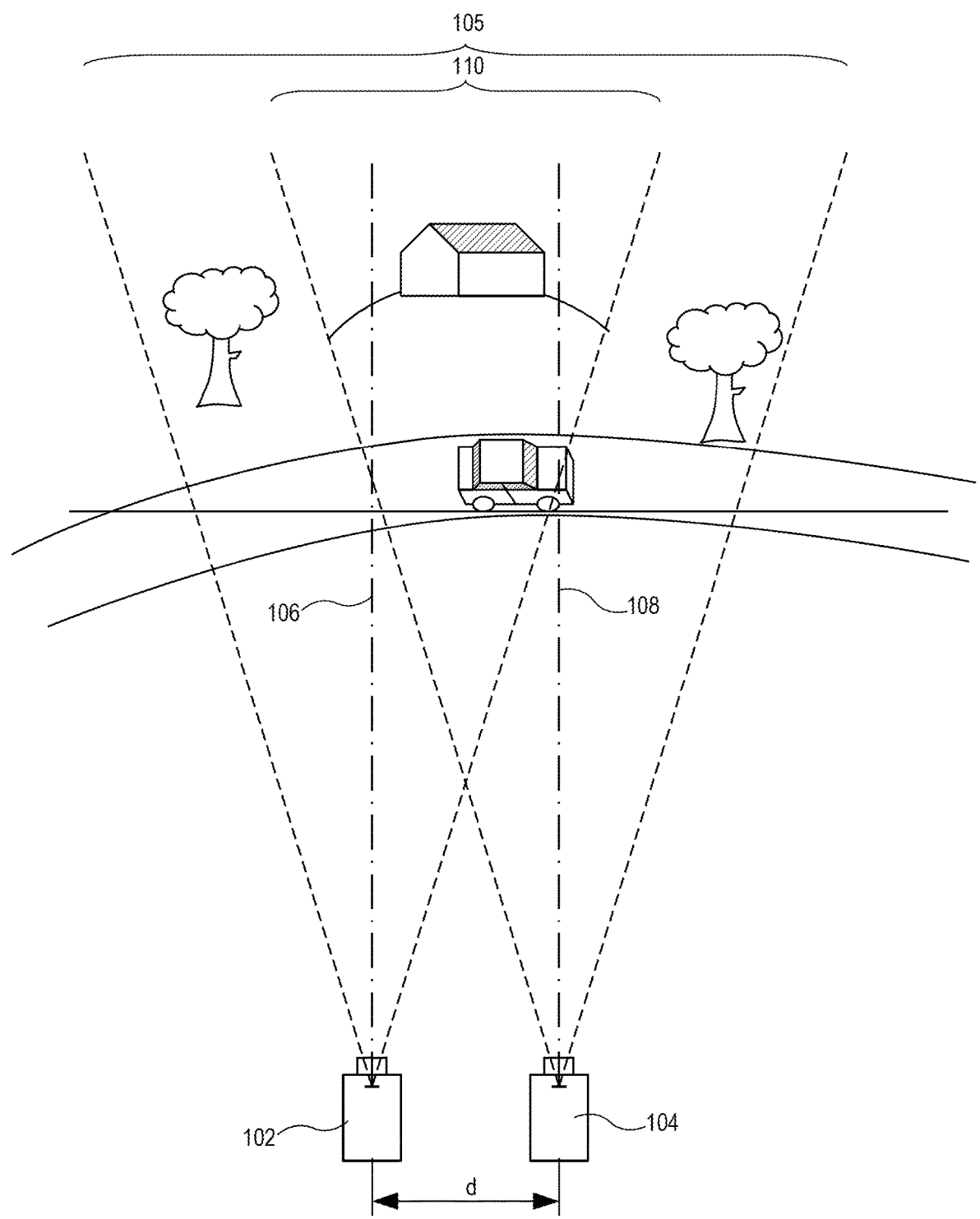
FIG. 1 is a schematic view of a setup using two cameras to increase the width of the scene covered by a camera system.
Figure 2:
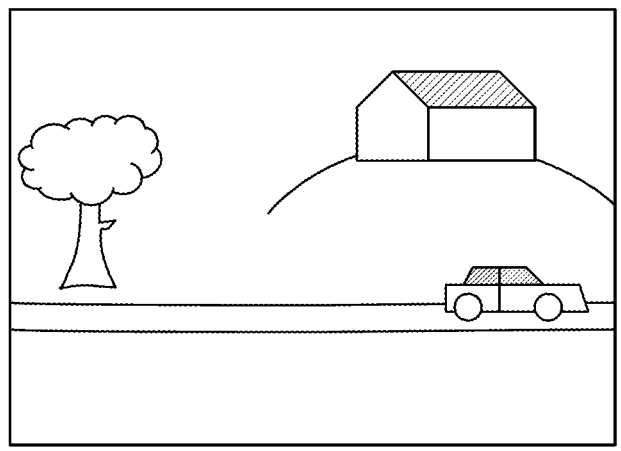
FIG. 2 is a schematic view of the scene captured by camera 102 in FIG. 1.
Figure 3:
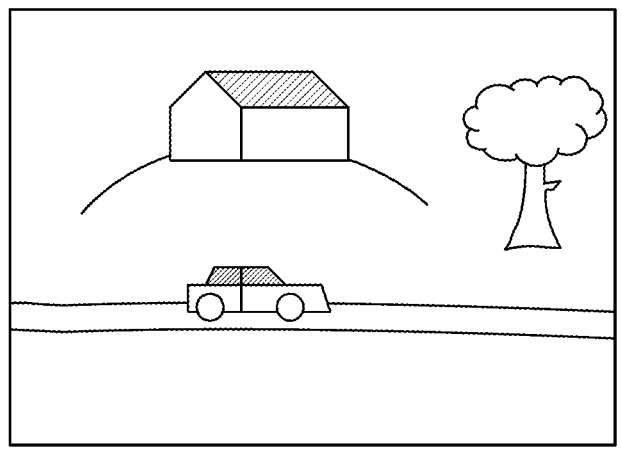
FIG. 3 is a schematic view of the scene captured by camera 104 in FIG. 1.
Figure 4:
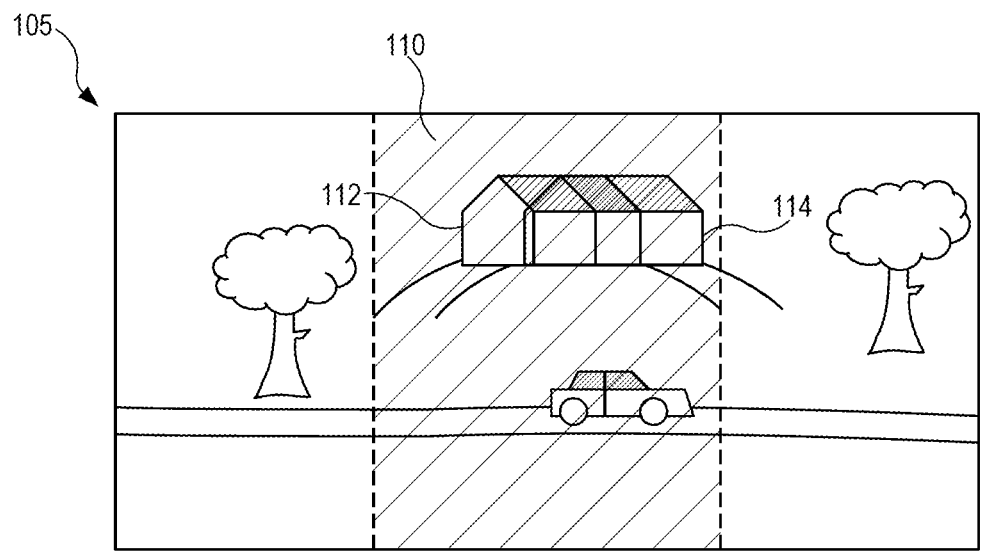
FIG. 4 is a schematic view of the two scenes of FIGS. 2-3 stitched together and aligning the road/car of the scene so that no parallax is present for the objects in that region.

In order to avoid parallax artefacts for the object 512, the projection surface 516 had to be moved to intersect the position of the object. However, other objects in the overlap region of the two camera views which are positioned at other distances from the origin, will show parallax effects. If the object 512 is the object of interest it may be a good enough representation of the overlap area that the object of interest does not experience parallax and the arrangement may present a good viewing experience for an operator or viewer. This may, as suggested above, be achieved by simply changing the distance to the projection surface 516 and such a feat may be accomplished using relatively little processing power as the projecting operation is a comparably simple operation. The effect is also depicted in FIGS. 1 and 4, where the projection surface is set at the distance from the camera system of the road and the house in the background shows parallax artefacts.

Figure 8:
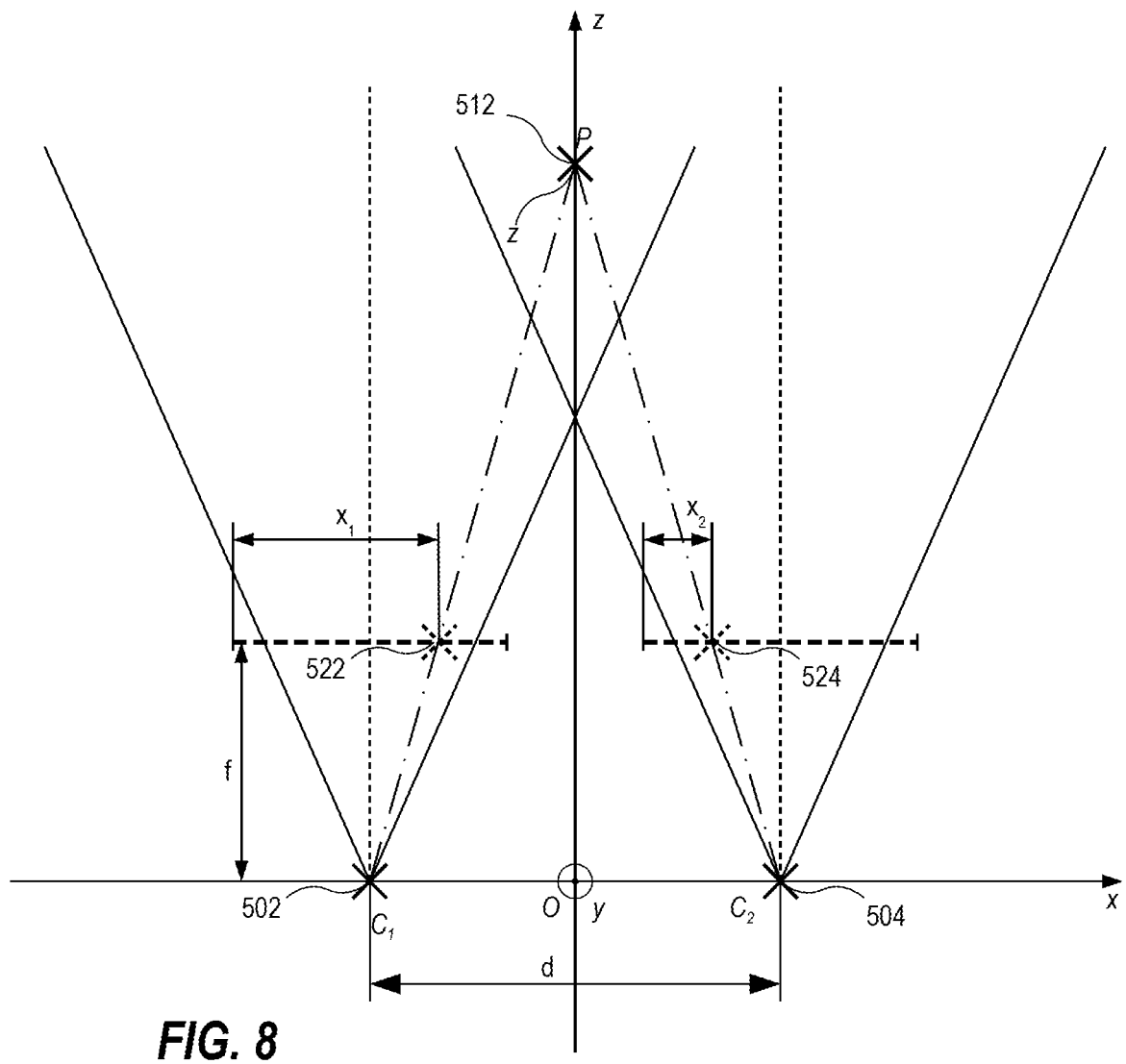
FIG. 8 is a schematic view of features used in a triangulation method based on disparity of feature positions.

The distance to the object 512, i.e. position P from the origin O, may be obtained using known methods, e.g. a geometric triangulation method based on known properties of the system and analysis of captured image data, active distance measuring such as radar, lidar, time of flight (TOF) technology. In one specific example of geometric triangulation the depth is calculated based on disparity between a feature present in each of the images, see FIG. 8. The distance z to the object from the origin O may be calculated using the disparity, $x_1$-$x_2$, and equation 1:

$$x_1 - x_2 = \frac{df}{z} \qquad \text{eq. 1}$$

The variable d in equation 1 is the distance between the cameras, which is known. The variables $x_1$ and $x_2$ are a distance in respective image at focal plane from an edge of image to a specific feature present in respective image, which may be measured in the captured images. The focal length f of the cameras is also known. Hence, the distance z to a specific feature from the origin O may be calculated using a rearrangement of equation 1, see equation 2:

$$z = \frac{df}{x_1 - x_2} \qquad \text{eq. 2}$$

Further, in some embodiments each camera 502, 504, includes a motion detector 520. The motion detector 520 is configured to detect motion in the captured scene and transmit properties of the detected motion to the image processing device 506. Alternatively, a motion detector 520 may be arranged in the image processing device 506 for detecting motion in the image streams from the cameras 502, 504, respectively. The motion detector 520 may be any motion detector or object tracker known to the person skilled in the art, e.g. a motion detection process based on video analytics. Examples on motion detection processes based on video analytics are object tracking implementing Dense Optical flow algorithms, Sparse optical flow algorithms, Kalman filtering, Meanshift algorithms, Camshift algorithms, Single object trackers, or Multiple object track finding algorithms. Implementations of some of these trackers are available in an open source computer vision and machine learning software library named OpenCV, https://opencv.org/. The properties of the detected motion may include the position of the motion. The position of the motion may be defined as a single point located at the center of mass of the detected objects, as an area of pixels representing the detected objects in combination with the position of the area, or as a position of a distinguishing feature being part of the detected motion.

According to some embodiments the distance from the projection surface 516 to the origin O is calculated to this position of the detected motion, this distance is referred to as the activity distance. The position of the detected motion may be identified in the image data from each of the cameras 502, 504. This distance may be continuously updated, i.e. the projection surface will be continuously adapted to objects in motion in the overlap region or it may be periodically updated, i.e. updated once every hour, etc.

According to other embodiments the positions of detected motions during a predetermined time period is stored and used to form a heat map. The average distance to the position including most frequent motion represented in the heat map may be used to calculate the distance to the projection surface 516 or the average distance to the positions registering most motion may be used to calculate distance to the projection surface 516. In this way the objects of interest for the purpose of stitching the images will be features or objects that moves in the scene.

According to yet other embodiments the motion in the overlap region of the camera views may be detected using a radar arranged nearby the camera system. If the motion detection is performed using a radar, a distance to the object in motion may be transferred to the image processing device 506 and used to set the distance for the projection surface 516 to the origin O in the three-dimensional coordinate system of the camera system 500.

Alternatively, the motion in the overlap region 110 of the camera views is detected and an image area in the image streams from each of the cameras 502, 504, is identified. Then a common image feature belonging to the detected motion is identified in the image area of the detected motion. The distance to the motion may then be calculated using this feature as the common reference point of the image data from the respective cameras 502, 504.

Figure 9:
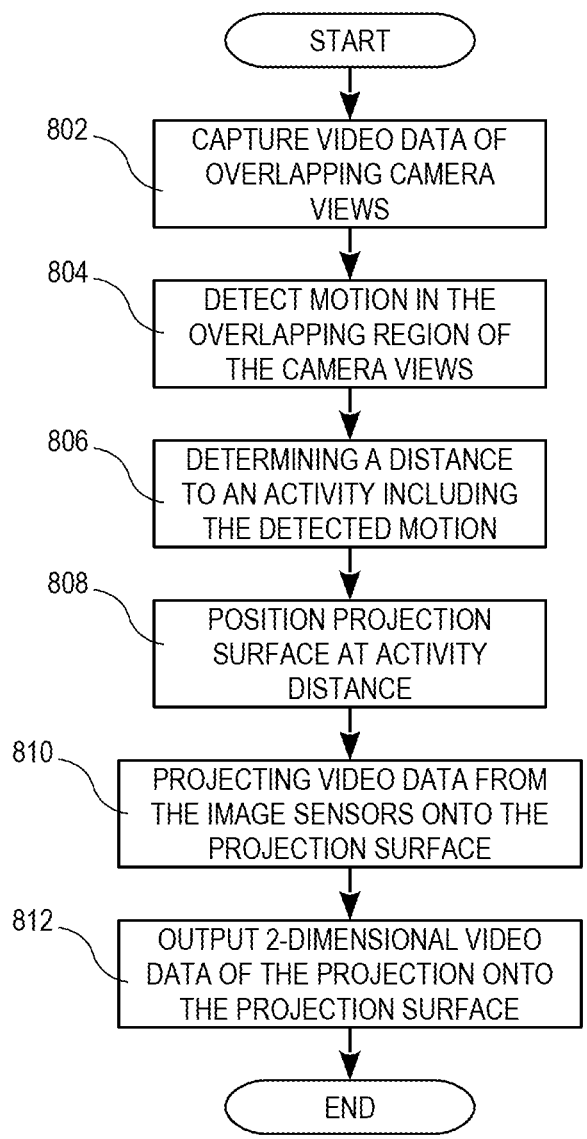
FIG. 9 is a flowchart of a process for generating stitched images according to embodiments.

Now referring to FIG. 9, one method of stitching video according to some embodiments start by having at least two cameras 502, 504, capturing video data of this scene in an overlapping fashion, step 802. As mentioned previously capturing overlapping video data includes having a portion of the captured video data of a first video camera representing a corresponding portion 110 of the total captured scene as a portion being captured by a second video camera.

A motion detection operation is performed on image data representing the overlapping camera views 110, step 804. The motion detection operation may initially be performed on video data from one of the cameras 502 capturing image data representing the overlapping camera views 110. Then the detected motion may be confirmed in video data from the other camera 504 capturing image data representing the overlapping camera views 110. Alternatively, the motion detection operation is only performed in image data from one of the cameras 502 and a common feature of the motion is identified in both sets of image data. Alternatively, the motion detection operation is performed in image data from both the cameras 502, 504, and then corresponding motion detection in both sets of image data is identified as one and the same motion. Then, the image data in which the motion is detected may be directly labeled as an activity or may be labeled as an activity when additional conditions are fulfilled. One such condition may be that a predetermined time period has expired.

The activity may then be the accumulated motion during the time period, e.g. a heatmap. Such a time period may be as long as a couple of months to a couple of hours. Another condition may be that a predetermined number of motion detections have been made. The number of motion detections that suffice for getting a useful result may vary due to the classification of a motion event, variation of the distance between various motion detections, etc. From the accumulated motion a position may be determined, as described earlier. The distance to the activity is then determined, step 806. The distance may be calculated as described above.

Then a predetermined projection surface 516, as described above, is positioned or repositioned at the determined activity distance, step 808. The image data captured from the image sensors 510 is then projected onto the projection surface 516, step 810. Various processes for projecting the image data from one or a plurality of cameras onto a projection surface 516 are well known top the person skilled in the art. One description of such processes is found in "Multiple View Geometry in Computer Vision", Second Edition 2003, by Richard Hartley and Andrew Zisserman.

By projecting the image data from the image sensors 510 onto the projection surface 516 that is positioned at the determined activity distance z the parallax at the position of the activity may be avoided at a lower cost than if the entire overlap area 110 was to be recalculated for avoiding parallax in the entire overlap area 110. The stitched video is now represented on the projection surface 516 and the data may be outputted from the projection video as two-dimensional video data, step 812, to be encoded and/or displayed. As the video data projected on the projection surface 516 represents the two video streams stitched together the output from the above process will be the stitched video streams.

The process may be implemented so that when the distance to the projection surface 516 has been determined, the stitching of the video from the two image sensors 510 may include projecting the image data from each of the image sensors onto the projection surface 516 at the determined activity distance z for as long as the process do not get any indication that the distance should be updated. One example of such an indication may be that the process evaluates the activity distance continuously and when the calculated activity distance differs from the activity distance presently used for the projection surface 516 with a value larger than a predetermined distance threshold the activity distance used for the projection surface 516 is updated.

A simple but effective way to combine the two videos in the overlap area 110 is to arrange the process to blend the image information in that area. For instance, each position of the overlap on the projection surface 516 may be given an intensity in each of the color channels resulting from adding half of the intensity, e.g. alpha blending in the position from one of the image sensors 510 to half of the intensity in the position from the other image sensor. Further methods for combining the image data in the overlap region are well known to the person skilled in the art, some of them are available in OpenCV, e.g. FeatherBlender and MultiBandBlender.

The identification of the position of the activity that is used for determining the distance to the projection surface 516 may be calculated in a couple of different ways, as indicated in the above description. According to one embodiment the determination of the activity distance z includes detecting motion in the video from one camera 502 of the two cameras 502,504 and determine the position of that motion within the camera view of the camera 502. Detecting motion in the video from the other camera 504 and determine the position of that motion within the camera view of the camera 504. Correlating the motion detected in the camera view of camera 502 with the motion detected in the camera view of camera 504 determining if the motion detected in the video of the camera view of camera 502 is the same motion as detected in the video of the camera view of camera 504. The correlation of the two detected motions may be based on any one or any combination of the features in the group including the position of the motion, i.e. position in the overlap area 110 of the two camera views, time of each motion, i.e. the motions are detected at approximately the same time, velocity of the detected motion, i.e. are the velocity of the detected motions the same, or direction of the detected motion, i.e. are the direction of the motion the same. When it is determined that the detected motions in each of the video streams from the cameras 502, 504, belongs to the same activity then the activity distance z to the position of the motion may be calculated as described earlier and the projection surface 516 may be positioned at the calculated activity distance. The motion and the object responsible for the motion may be tracked and the activity distance may be updated periodically during its movement. Alternatively, the calculation of the activity distance is performed periodically as long as motion is detected. In yet another alternative the activity distance is periodically calculated and is the calculated activity distances are accumulated and a mean value for the activity distance may be calculated. In a slightly different approach the accumulation of activity distances only includes the latest ten, hundred, or thousand activity distances.

In another alternative approach a heatmap indicating the position in the overlap area of the camera views where motion is detected most frequently is generated, and may be continuously added to. One heatmap for each of the video streams from the cameras are generated and then the position experiencing the greatest number of motion detections in each of the video streams is determined to relate to the same activity and therefore the positions in each of the camera streams is used in the calculation of the activity distance, as described earlier.

The present claims may be directed to a camera system, a method, and/or a computer program product at any possible technical detail level of integration. The computer program product may include a computer readable storage medium (or media) having computer readable program instructions thereon for causing a processor to carry out aspects.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects herein.

Aspects have been described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for stitching video data from two image sensors arranged to each capture video data of overlapping camera views of a scene, the method comprising:
    capturing video data of overlapping camera views of the scene using two image sensors, each image sensor having a position in a three-dimensional coordinate system relative to an origin of the three-dimensional coordinate system;
    detecting motion in an area in the camera views corresponding to the overlapping camera views;
    determining an activity distance, the activity distance being the distance from a position corresponding to the origin of the three-dimensional coordinate system to an activity position that includes the detected motion;
    positioning, in the three-dimensional coordinate system, a projection surface having a predetermined shape at a position having a distance from the origin of the three-dimensional coordinate system corresponding to the determined activity distance, wherein the projection surface is positioned so that the projection surface intersects a position in the three-dimensional coordinate system corresponding to the activity position;
    projecting the video data from each of the image sensors onto the projection surface; and
    outputting a two-dimensional video corresponding to the projected video data.

2. A method according to claim 1, wherein the detecting motion in an area in the camera views corresponding to the overlapping camera views includes detecting moving pixels in an overlapping portion of the captured video.

3. A method according to claim 1, further comprising determining from pixel data in the overlapping camera views the activity position of the detected motion and using this activity position in the determining of the activity distance.

4. A method according to claim 1, wherein the determining of the activity distance is based on a momentaneous instance of the detected motion in the overlapping image data and setting the position of the motion as the activity position.

5. A method according to claim 1, wherein the determining of an activity distance includes accumulating motion data in the overlapping image data during a predetermined time period and then selecting a position that have accumulated most motion during this time period as the activity position.

6. A method according to claim 1, wherein determining the activity distance includes comparing the position of the activity position in the captured video data with corresponding positions in a predetermined table including distances to positions in a coordinate system of each of the image sensors.

7. A method according to claim 1, wherein determining the activity distance includes receiving a radar signal covering the overlapping scenes, correlating a radar response to the activity position, and retrieving the distance to the activity position from the radar signal.

8. A method according to claim 1, wherein determining the activity distance includes calculating the difference, $x_1-x_2$, in position of the activity position in the captured images from the two sensors.

9. A method according to claim 1, wherein the projection surface is a plane.

10. A method according to claim 1, wherein the projection surface is a cylindrical surface.

11. A method according to claim 1, wherein the projection surface is a spherical surface.

12. A camera system comprising:
two cameras, each including an image sensor having a position in a three-dimensional coordinate system relative to an origin of the three-dimensional coordinate system, configured to capture video data of overlapping camera views of a scene;
at least one image processing device;
a predetermined projection surface defined in the three-dimensional coordinate system;
a motion detector configured to detect motion in an area in the camera views corresponding to the overlapping camera views of the two cameras;
a processor configured to determine an activity distance, the activity distance being the distance from a position corresponding to the origin of the three-dimensional coordinate system to an activity position that includes the detected motion;
an image projector configured to project the video data from each of the cameras onto the projection surface, wherein the projection surface is positioned in the three-dimensional coordinate system at a position having a distance from the origin of the three-dimensional coordinate system corresponding to the determined activity distance, wherein the projection surface is positioned so that the projection surface intersects a position in the three-dimensional coordinate system corresponding to the activity position; and
an output configured to output a two-dimensional video corresponding to the projected video data.

13. A camera system according to claim 12, wherein the motion detector is configured to detect moving pixels in the overlapping portion of the video data from the cameras.

14. A camera system according to claim 12, further comprising a motion accumulator connected to the motion detector for accumulating detected motions during a predetermined period of time and wherein the activity distance determining module is configured to determine the activity distance from the accumulated detected motions.

15. A camera system according to claim 12, wherein the image projector is configured to project video data onto a plane projection surface.

* * * * *